(12) United States Patent
Wessig et al.

(10) Patent No.: US 8,664,410 B2
(45) Date of Patent: Mar. 4, 2014

(54) FLUORESCENT DYE AND USE THEREOF

(75) Inventors: Pablo Wessig, Berlin (DE); Kristian Möllnitz, Berlin (DE); Robert Wawrzinek, Berlin (DE)

(73) Assignee: Universitat Potsdam, Postdam (DE)

( * ) Notice: Subject to any disclaimer, the term of this patent is extended or adjusted under 35 U.S.C. 154(b) by 207 days.

(21) Appl. No.: 13/168,288

(22) Filed: Jun. 24, 2011

(65) Prior Publication Data

US 2011/0319639 A1 Dec. 29, 2011

(30) Foreign Application Priority Data

Jun. 25, 2010 (EP) .................... 10167327

(51) Int. Cl.
| | |
|---|---|
| C07D 317/64 | (2006.01) |
| C07D 317/68 | (2006.01) |
| C07D 493/04 | (2006.01) |
| C07D 493/10 | (2006.01) |
| C07D 493/14 | (2006.01) |
| C07K 1/13 | (2006.01) |
| C09B 57/00 | (2006.01) |
| G01N 33/52 | (2006.01) |
| G01N 33/533 | (2006.01) |

(52) U.S. Cl.
USPC ............ 549/338; 549/383; 549/433; 549/436

(58) Field of Classification Search
None
See application file for complete search history.

(56) References Cited

FOREIGN PATENT DOCUMENTS

| CH | 696358 | 5/2007 |
| WO | WO91/12024 | 8/1991 |

OTHER PUBLICATIONS

Nakagawa et al., caplus an 2004:1068219.*
Dallacker et al., caplus an 1987:155966; 1987.*
Dallacker Franz et al., conversion of symmetrically substituted aromatic ethers into benzouinones, *Chemiker Zeitung, Wiley-VCH Verlag GmbH & Co.*, 110, Jahrgang (1986). XP009142534.
Dallacker et al., Derivate des Methylendioxybenzols, 34, Chemische Berichte, Bd. 104, Nr. 8, Aug. 1, 1971, XP002614625.
Dallacker et al., Metalation of symmetrically substituted aromatic ethers, Chemiker Zeitung, Wiley-VCH Verlag GmbH & Co., Bd. 110, Nr. 10, Jan. 1, 1986, XP009142673.
Orlemans et al., "tert-Amino effect" inHeterocyclic Synthesis. The Effect of a p-Quinone Moiety on the [1,6] H-Transfer and 1,5-Electrocyclization Reactions,*J. Org. Chem.*, 1988, 53, 2278-2287.

* cited by examiner

*Primary Examiner* — Sun Jae Loewe
(74) *Attorney, Agent, or Firm* — Enshan Hong; Kent H. Cheng; VLP Law Group LLP

(57) ABSTRACT

The invention relates to a fluorescent dye of general formula I or II

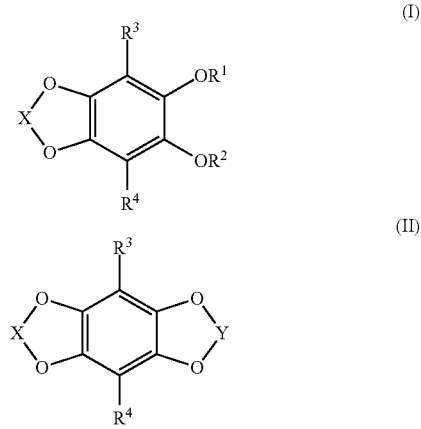

wherein $R^1$, $R^2$, $R^3$ and $R^4$ are independently hydrogen or a branched or unbranched, saturated or unsaturated, aliphatic or aromatic, functionally substituted, or unsubstituted hydrocarbon radical, wherein at least one of the $R^1$ or $R^2$ radicals and one of the $R^3$ or $R^4$ radicals is not hydrogen and the $R^1$ and $R^3$ radicals and/or $R^2$ and $R^4$ radicals in formula I can be bridged to each other, and X and Y independently represent a substituted or unsubstituted $C_1$ or $C_2$ hydrocarbon radical wherein any one carbon unit can be replaced by an N or S heteroatom. The dye is remarkable for its high fluorescence intensity and large Stokes shift in combination with a long fluorescence lifetime.

19 Claims, 3 Drawing Sheets

FLUORESCENT DYE AND USE THEREOF

Figure 1:
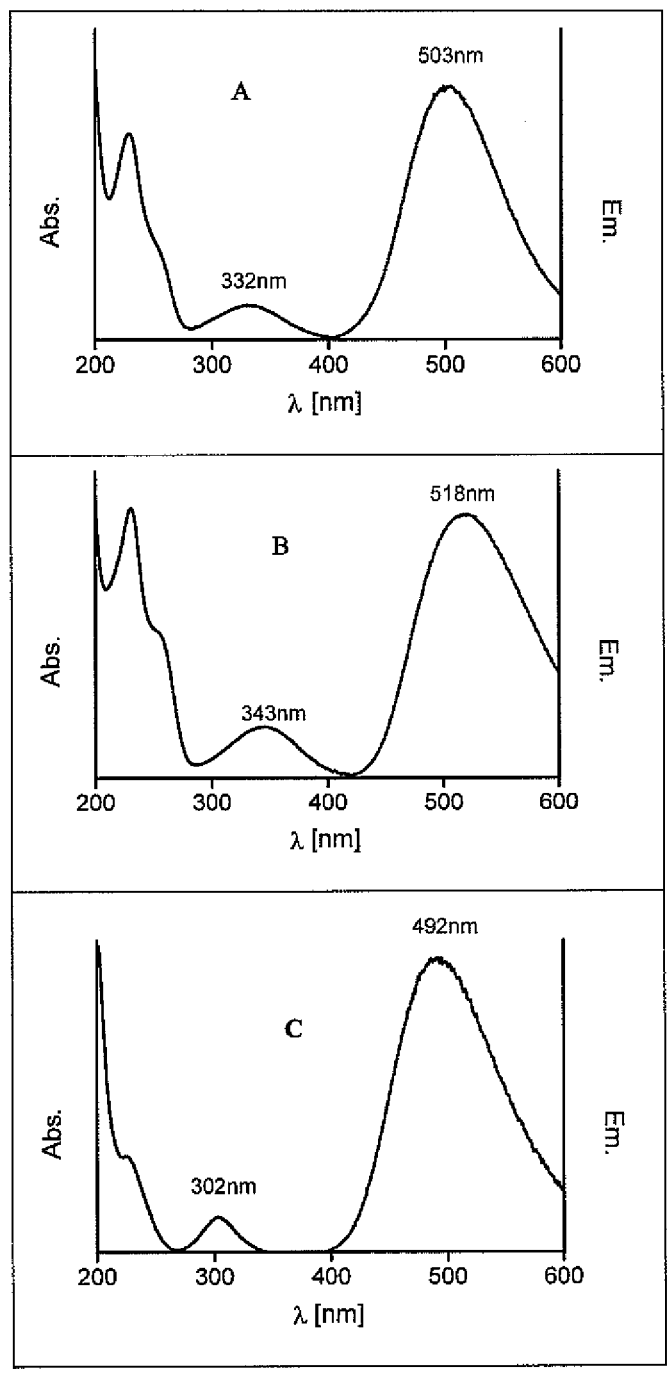

Priority is claimed on the following application: EP Application No.: 10167327.5 filed on Jun. 25, 2010, the content of which is incorporated here by reference.

FIELD OF THE INVENTION

The invention relates to a fluorescent dye based on a 1,2,4,5-tetrahydroxybenzene derivative, which dye has a long fluorescence lifetime and large Stokes shift, and also relates to the use of this compound as a fluorescent dye.

DESCRIPTION OF THE RELATED ART

Dyes which, when irradiated with light of a wavelength absorbed by these substances, emit light of a (usually) different wavelength are referred to as fluorescent dyes. These fluorescent dyes have been widely used in biochemistry, biology and medicine, e.g. in diagnostic kits, in microscopy or in drug screening.

From a structural aspect, fluorescent dyes are mostly based on aromatic structures, in particular fused heteroaromatic compounds. One group of fluorescent dyes is derived from xanthene, e.g. fluorescein, calcein, eosin or merbromin. Inter alia, xanthene-based dyes include rhodamines such as rhodamine B, rhodamine 6G, rhodamine 123, Texas Red, tetramethylrhodamine methyl ester (TMRM). Dyes such as Nile Blue or Nile Red are based on a related backbone structure, namely, benzophenoxazine. In addition, coumarin dyes such as coumarin itself, or umbelliferone; indole dyes such as 4',6-diamidine-2-phenylindole; phenanthridine dyes such as ethidium bromide or propidium iodide; benzofuran dyes such as furaptra or fura dyes; and benzothiazole dyes such as luciferin or SYBR Green I are well-known. Xylenol orange, berberine, epicocconone, IAEDANS or coelanterazine are based on various other heteroaromatic backbone structures. Cyanines (polymethine dyes), the most prominent members thereof being indocyanine green, Cy5 and Cy7, may also be mentioned.

Fluorescent dyes are characterized by a number of parameters allowing a user to select a suitable dye depending on the desired purpose. Primarily, this includes the excitation wavelength $\lambda_{exc}$ (or $\lambda_{abs}$), which corresponds to the maximum of the absorption band, the emission wavelength $\lambda_{em}$, which corresponds to the maximum of the emission band, the Stokes shift $\Delta\lambda$, which corresponds to the difference of emission wavelength $\lambda_{em}$ and excitation wavelength $\lambda_{exc}$, the extinction coefficient $\epsilon$, which represents the proportion of radiation absorbed at the wavelength of excitation, $\lambda_{exc}$, the fluorescence quantum yield $\Phi_F$, which corresponds to the quantity of emitted to absorbed photons, and the fluorescence lifetime $\tau_F$, which corresponds to the average time during which the molecule remains in its excited state before transition into its ground state by emission of a quantum of light occurs.

It is desirable, particularly with respect to biological applications, to have a large excitation wavelength $\lambda_{exc}$ so as to allow penetration of exciting radiation into biological samples as deep as possible, a large extinction coefficient $\epsilon$ so as to absorb a maximum of incident light, a large Stokes shift $\Delta\lambda$ so as to have lowest possible interactions between excitation and emission radiations, a long fluorescence lifetime $\tau_F$ so as to mask the natural short-lived background fluorescence of biological tissues, and, finally, a large fluorescence quantum yield $\Phi_F$ so as to achieve a high signal-to-noise ratio.

Well-known fluorescent dyes with relatively large Stokes shift ($\Delta\lambda \geq 100$ nm) typically have a relatively short fluorescence lifetime ($\tau_F \leq 5$ ns). Conversely, relatively small Stokes shifts ($\Delta\lambda \leq 50$ nm) are observed in well-known dyes having a long fluorescence lifetime ($\tau_F \geq 15$ ns). However, fluorescent dyes having large Stokes shift and long fluorescence lifetime at the same time are largely unknown.

The invention is based on the object of providing a fluorescent dye which satisfies the aforementioned requirements to the largest possible extent. In particular, the dye should have both long fluorescence lifetime and large Stokes shift.

Said object is accomplished by means of a fluorescent dye in accordance with claim 1. Other preferred embodiments of the dye can be inferred from the other features mentioned in the subclaims.

The fluorescent dye according to the invention corresponds to one of general formulas I or II:

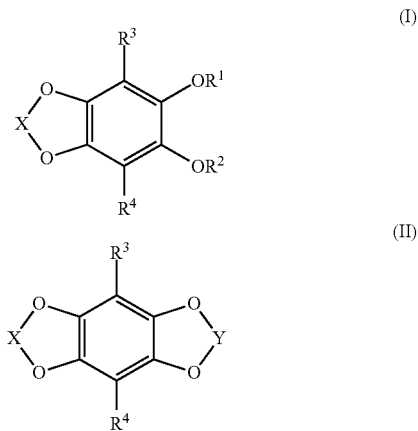

wherein
$R^1$, $R^2$, $R^3$ and $R^4$ are independently hydrogen or a branched or unbranched, saturated or unsaturated, aliphatic or aromatic, functionally substituted, or unsubstituted hydrocarbon radical, wherein at least one of the $R^1$ or $R^2$ radicals and one of the $R^3$ or $R^4$ radicals is not hydrogen and the $R^1$ and $R^3$ radicals and/or $R^2$ and $R^4$ radicals in formula I can be bridged to each other; and
X and Y independently represent a substituted or unsubstituted $C_1$ or $C_2$ hydrocarbon radical wherein any one carbon unit can be replaced by an N or S heteroatom.

An equivalent definition of the fluorescent dye according to the invention refers only to general formula I with the above definitions of the radicals, wherein $R^1$ and $R^2$ can be bridged to each other.

In formal terms, the fluorescent dye according to the present invention is derived from structure IV which in turn can be derived from 1,2,4,5-tetrahydroxybenzene according to formula III.

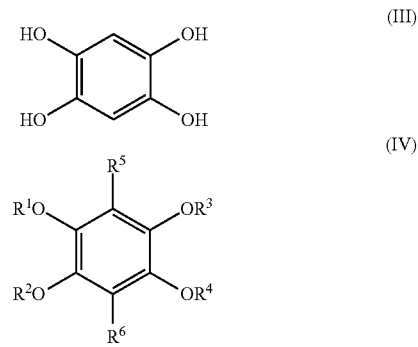

Compounds of structure IV wherein the radicals $R^1$ to $R^4$ are not linked (bridged) to each other and wherein the radicals $R^5$ and $R^6$ are electron acceptors (e.g. acyl groups) have been described in the literature. These compounds show no fluorescence at all, and there are no indications that such compounds could be useful as fluorescent dyes. The present inventors have found, however, that bridging of one pair of adjacent hydroxyl groups or alkoxy groups by a group X (compounds of type I) or of both pairs of adjacent hydroxyl groups or alkoxy groups by the groups X or Y (compounds of type II) results in an unexpected intense fluorescence in combination with an exceptionally large Stokes shift and long fluorescence lifetime.

More specifically, the difference between the longest wavelength maximum of the absorption spectrum and the shortest wavelength maximum of the emission spectrum (Stokes shift) is at least 80 nm, especially at least 100 nm, preferably even at least 150 nm. Quite exceptionally, the dyes according to the invention simultaneously have a long fluorescence lifetime of at least 5 ns, in particular of at least 15 ns, and preferably even at least 20 ns. Another advantage is their high fluorescence intensity which can be seen in fluorescence quantum yields of at least 0.2 (20%), especially of at least 0.4 (40%), and preferably of at least 0.5 (50%).

In the general formulas I and II the radicals $R^3$ and $R^4$ are preferably selected to be the same. Alternatively or simultaneously, the radicals $R^1$ and $R^2$ in the structure according to formula I can be selected to be the same.

In principle, the radicals $R^1$, $R^2$, $R^3$ and $R^4$ can be provided with any chain length, e.g. in the form of alkyl, aryl, alkenyl, alkynyl, alkoxy, ether, alkoxyether, acyl, ketone, carboxylic acid, carboxylic ester, aldehyde and mixed forms thereof, particularly up to $C_{50}$ units, preferably up to $C_{40}$ units, more preferably up to $C_{30}$ units, optionally including further heteroatoms and/or low-molecular weight functional groups. According to an advantageous embodiment, the radicals $R^1$, $R^2$, $R^3$ and $R^4$ can independently represent in particular a branched or unbranched, saturated or unsaturated, functionally substituted, or unsubstituted $C_1$-$C_{20}$ alkyl radical, $C_5$-$C_{20}$ aryl radical, $C_2$-$C_{20}$ alkenyl radical, $C_2$-$C_{20}$ alkynyl radical, $C_1$-$C_{20}$ alkoxy radical, $C_2$-$C_{20}$ ether radical, $C_2$-$C_{20}$ alkoxyether radical, $C_2$-$C_{20}$ acyl radical, $C_3$-$C_{20}$ ketone radical, $C_1$-$C_{20}$ carboxylic acid radical, $C_2$-$C_{20}$ carboxylic ester radical, or $C_1$-$C_{20}$ aldehyde radical or a mixed form thereof. These radicals are preferably selected among branched or unbranched, saturated or unsaturated, functionally substituted, or unsubstituted $C_1$-$C_{15}$ alkyl radicals, $C_5$-$C_{15}$ aryl radicals, $C_2$-$C_{15}$ alkenyl radicals, $C_2$-$C_{15}$ alkynyl radicals, alkoxy radicals, $C_2$-$C_{15}$ ether radicals, $C_2$-$C_{15}$ alkoxyether radicals, $C_2$-$C_{15}$ acyl radicals, $C_3$-$C_{15}$ ketone radicals, $C_1$-$C_{15}$ carboxylic acid radicals, $C_2$-$C_{15}$ carboxylic ester radicals, or $C_1$-$C_{15}$ aldehyde radicals or mixed forms thereof. Branched or unbranched, saturated or unsaturated, functionally substituted, or unsubstituted $C_1$-$C_{10}$ alkyl radicals, $C_5$-$C_{10}$ aryl radicals, $C_2$-$C_{10}$ alkenyl radicals, $C_2$-$C_{10}$ alkynyl radicals, $C_1$-$C_{10}$ alkoxy radicals, $C_2$-$C_{10}$ ether radicals, $C_2$-$C_{10}$ alkoxyether radicals, $C_2$-$C_{10}$ acyl radicals, $C_3$-$C_{10}$ ketone radicals, $C_1$-$C_{10}$ carboxylic acid radicals, $C_2$-$C_{10}$ carboxylic ester radicals or $C_1$-$C_{10}$ aldehyde radicals or mixed forms thereof are particularly preferred.

In the case of $R^3$ and $R^4$, acyl radicals of the above definitions are particularly preferred.

The optional bridging between the radicals $R^1$ and $R^3$ and/or the radicals $R^2$ and $R^4$ in general formula I or II preferably results in a 4- to 7-membered ring, in particular a 5- to 6-membered ring, and a 6-membered ring is particularly preferred (see dye G below).

In the context of the present invention, "functionally substituted" is understood to be replacement of one or more hydrogens of the hydrocarbon radicals by low-molecular weight functional groups such as sulfonic, sulfhydryl, sulfate, sulfite, phosphoric, phosphate, nitro, nitrate, nitrite, amino, amide, hydroxy, silyl, alkoxy groups and/or halogen atoms.

According to a particularly advantageous embodiment of the invention, at least one of the radicals $R^3$ and $R^4$ in the structures I and II, and in particular both radicals $R^3$ and $R^4$ represent an electron acceptor, which term describes a radical that reduces the electron density on the central benzene ring. More specifically, the radicals $R^3$ and/or $R^4$ can be a nitro group, a $C_2$-$C_{20}$ acyl radical, $C_2$-$C_{20}$ acylaryl radical, $C_2$-$C_{20}$ acylalkenyl radical, or $C_2$-$C_{20}$ acylalkynyl radical, and these radicals can be substituted in particular with "electron-attracting" groups such as nitro groups. In a preferred fashion the radicals $R^3$ and/or $R^4$ represent a nitro group, a $C_2$-$C_{15}$ acyl, acylaryl, acylalkenyl, or acylalkynyl radical and more preferably a $C_2$-$C_{10}$ acyl, acylaryl, acylalkenyl or acylalkynyl radical. In specific embodiments the radicals $R^3$ and/or $R^4$ represent a methylacyl radical, an ethylacyl radical, a propylacyl radical, a tert-butylacyl radical, an n-propylacyl radical.

Advantageously, the bridging radicals X and Y in the general formulas I and II independently represent a substituted or unsubstituted $C_1$ hydrocarbon radical, in particular a $CH_2$ radical, $CHR^5$ radical or $CR^5R^6$ radical. In general, the radicals $R^5$ and $R^6$ can be selected from the groups mentioned above for the radicals $R^1$ to $R^4$, and $R^5$ and $R^6$ can also be bridged to each other to form in particular a 3- to 6-membered spiro ring. In specific embodiments the radicals X and Y are selected to be a methyl radical (see dyes A-C, E, F below), a spirocyclohexyl radical (see dye D below) or 1-alkoxycarbonyl-1-alkoxycarbonylmethylmethylene (see dyes E, F below).

At least one of the radicals $R^1$ and $R^2$ and in particular both radicals $R^1$ and $R^2$ in general formula I can preferably be selected from the group consisting of a $C_1$-$C_{20}$ alkoxy radical, $C_2$-$C_{20}$ ether radical, $C_2$-$C_{20}$ alkoxyether radical. More specifically, $C_1$-$C_{15}$ alkoxy radicals, $C_2$-$C_{15}$ ether radicals, $C_2$-$C_{15}$ alkoxyether radicals are possible. In a particularly preferred fashion, $R^1$ and/or $R^2$ are selected from $C_1$-$C_{10}$ alkoxy radicals, $C_2$-$C_{10}$ ether radicals, $C_2$-$C_{10}$ alkoxyether radicals.

Particularly preferred examples of fluorescent dyes according to the invention correspond to formulas A through G:

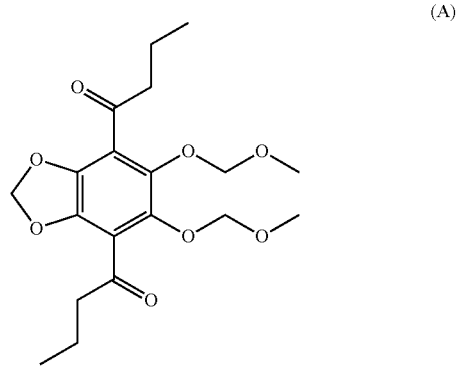

(A)

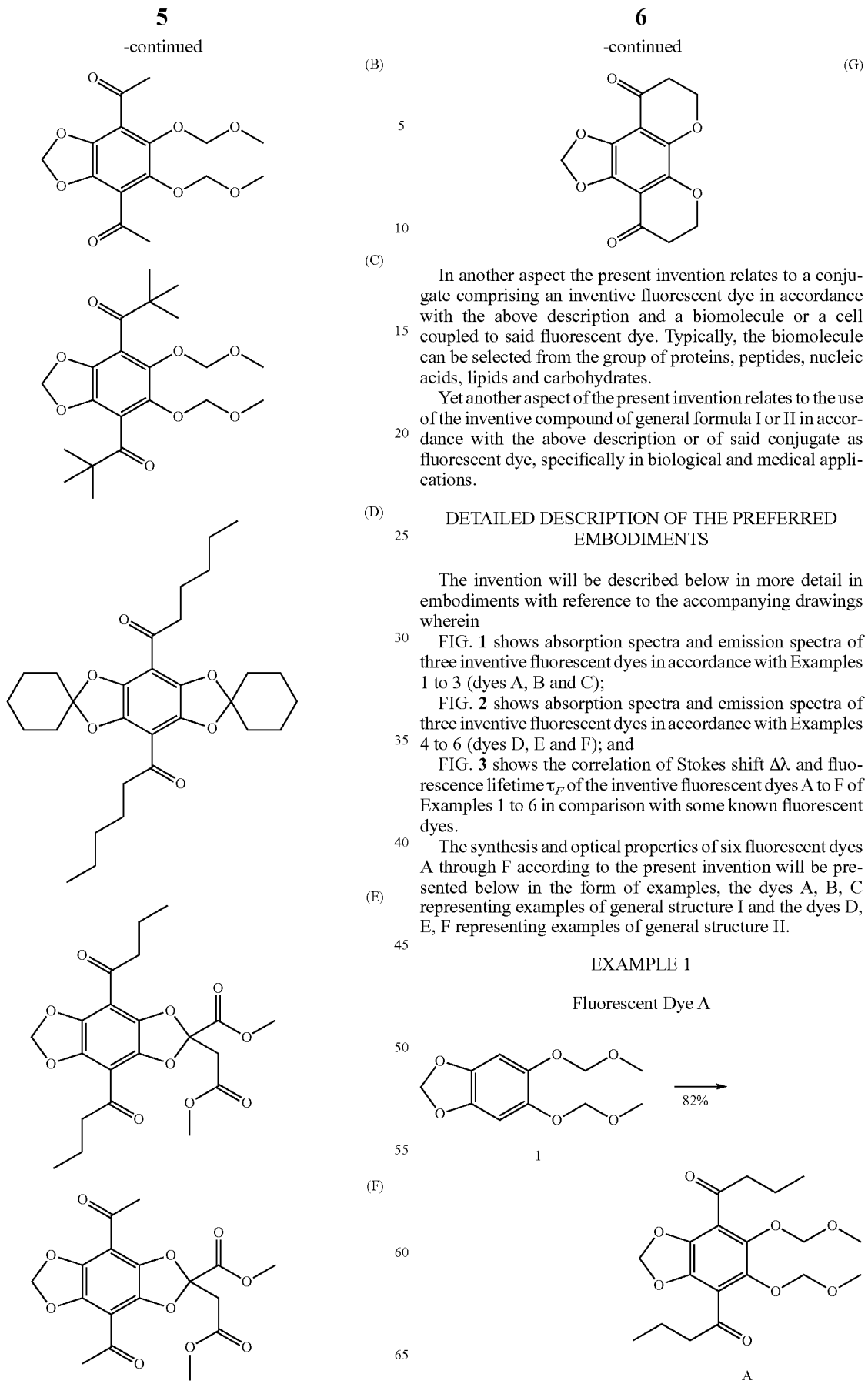

In another aspect the present invention relates to a conjugate comprising an inventive fluorescent dye in accordance with the above description and a biomolecule or a cell coupled to said fluorescent dye. Typically, the biomolecule can be selected from the group of proteins, peptides, nucleic acids, lipids and carbohydrates.

Yet another aspect of the present invention relates to the use of the inventive compound of general formula I or II in accordance with the above description or of said conjugate as fluorescent dye, specifically in biological and medical applications.

DETAILED DESCRIPTION OF THE PREFERRED EMBODIMENTS

Figure 2:
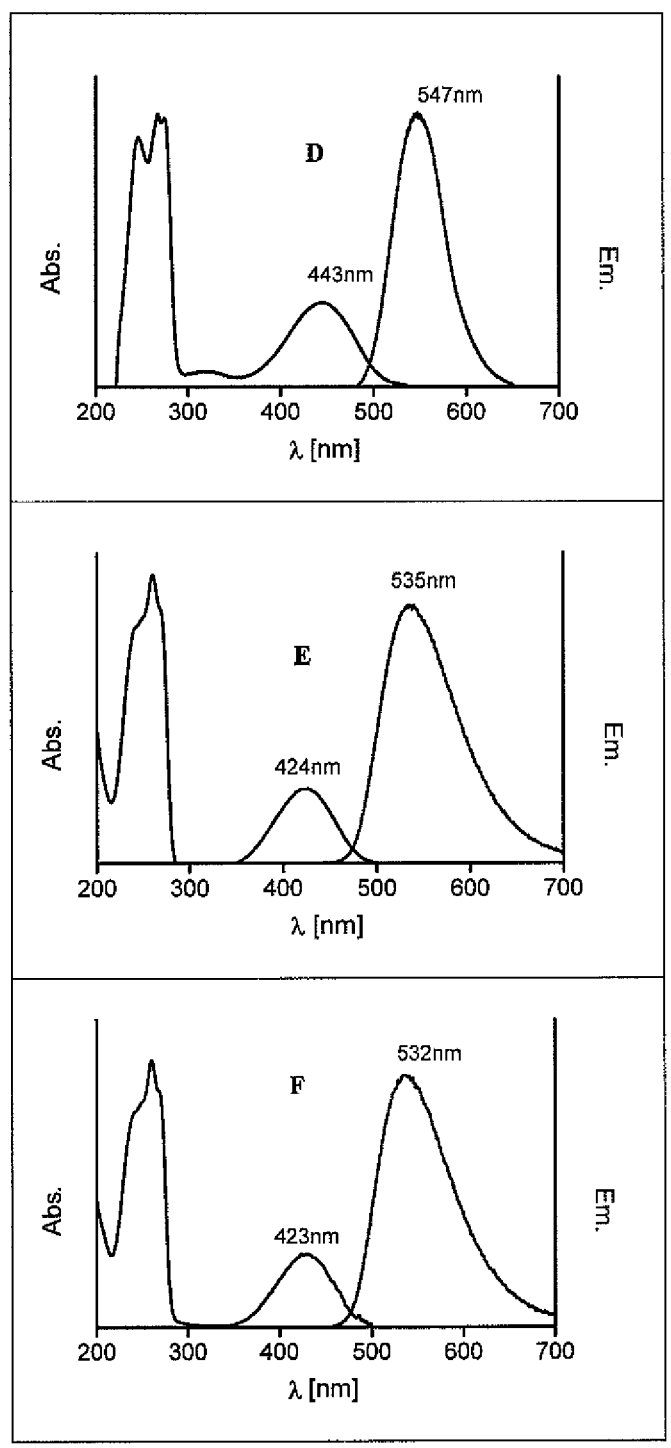
Figure 3:
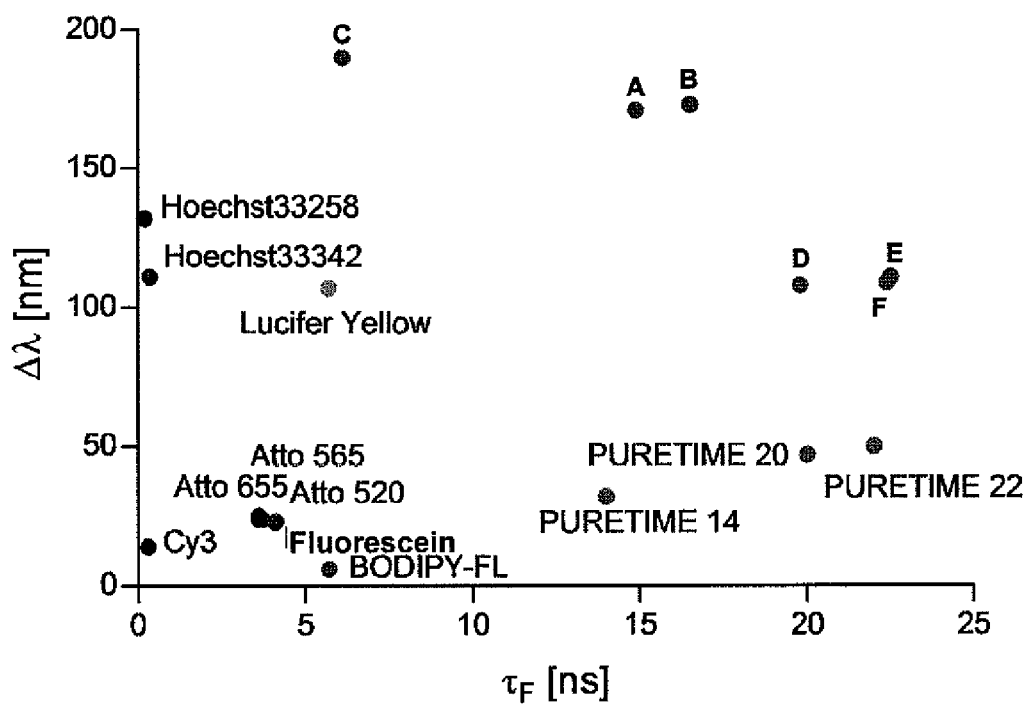

The invention will be described below in more detail in embodiments with reference to the accompanying drawings wherein FIG. 1 shows absorption spectra and emission spectra of three inventive fluorescent dyes in accordance with Examples 1 to 3 (dyes A, B and C);

FIG. 2 shows absorption spectra and emission spectra of three inventive fluorescent dyes in accordance with Examples 4 to 6 (dyes D, E and F); and FIG. 3 shows the correlation of Stokes shift $\Delta\lambda$ and fluorescence lifetime $\tau_F$ of the inventive fluorescent dyes A to F of Examples 1 to 6 in comparison with some known fluorescent dyes.

The synthesis and optical properties of six fluorescent dyes A through F according to the present invention will be presented below in the form of examples, the dyes A, B, C representing examples of general structure I and the dyes D, E, F representing examples of general structure II.

EXAMPLE 1

Fluorescent Dye A 3559 mg (14.69 mmol) of compound 1 was placed in 250 ml of dry THF. To this was added dropwise 24 ml (38.4 mmol) of n-butyl lithium (1.6 M), followed by addition of 7 g (36.76 mmol) of CuI. The suspension was subsequently added with 6.1 ml of butyric acid chloride and stirred at RT. This was added with saturated NH₄Cl solution, extracted with Et₂O, the combined organic phases were dried with MgSO₄, and the solvent was removed. Purification using LC afforded 4628 mg (12.1 mmol, 82%) of compound A in the form of a yellow solid.

EXAMPLE 2

Fluorescent Dye B

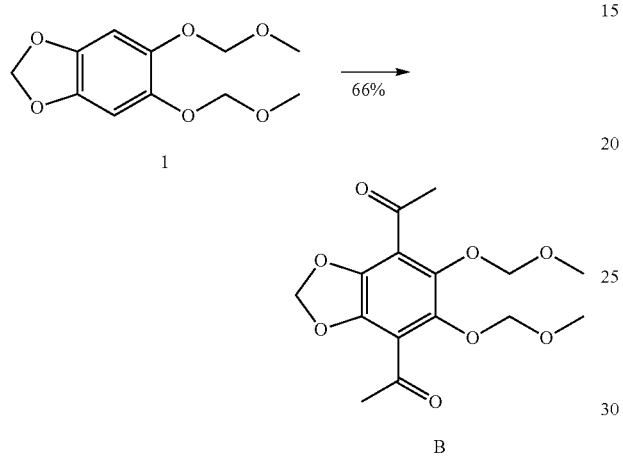

300 mg (1.24 mmol) of compound 1 was placed in 30 ml of dry THF. To this was added dropwise 2 ml (3.22 mmol) of n-butyl lithium (1.6 M), followed by addition of 590 mg (3.1 mmol) of CuI. The suspension was subsequently added dropwise with 0.65 ml (5.57 mmol) of acetyl chloride and stirred at RT. This was added with saturated NH₄Cl solution, extracted with Et₂O, the combined organic phases were dried with MgSO₄, and the solvent was removed. Purification using LC afforded 265 mg (0.81 mmol, 66%) of compound B in the form of a yellow solid.

EXAMPLE 3

Fluorescent Dye C

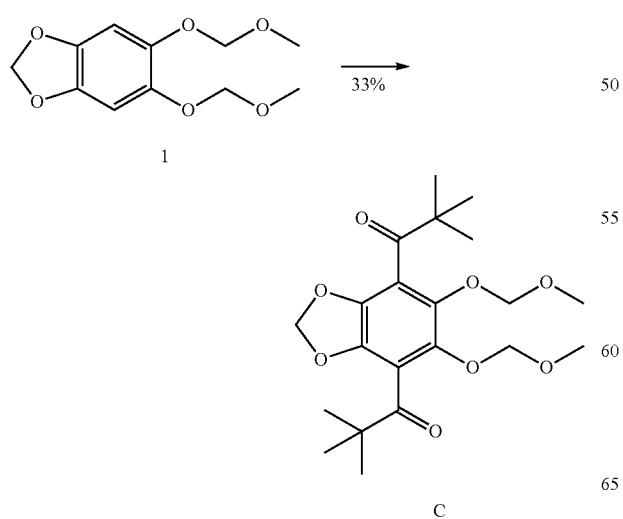

200 mg (0.8 mmol) of compound 1 was placed in 30 ml of dry THF. To this was added dropwise 1.35 ml (2.16 mmol) 24 ml (38.4 mmol) of n-butyl lithium (1.6 M), followed by addition of 393 mg of CuI. The suspension was subsequently added dropwise with 0.46 ml of pivaloyl chloride and stirred at RT. This was added with saturated NH₄Cl solution, extracted with Et₂O, the combined organic phases were dried with MgSO₄, and the solvent was removed. Purification using LC afforded 112 mg (0.27 mmol, 33%) of compound C in the form of a white solid.

EXAMPLE 4

Fluorescent Dye D

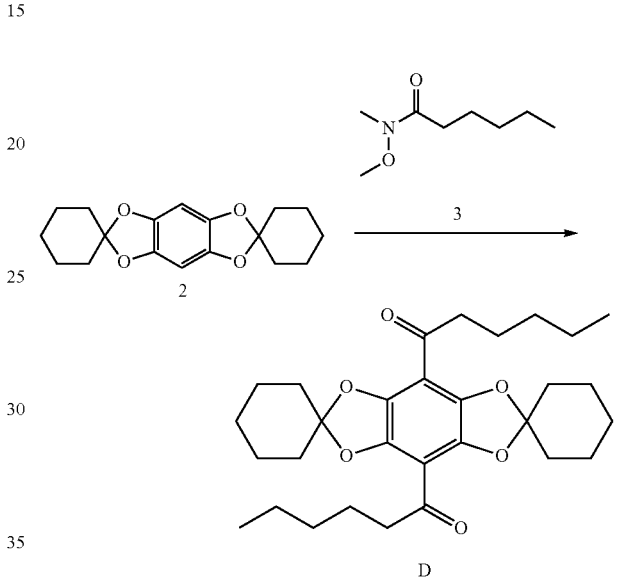

Compound 2 (3.69 g, 12.20 mmol) was placed in dry THF under protective gas, followed by addition of TMEDA (3.7 ml, 24.8 mmol, 2.0 eq.) and n-butyl lithium (16.8 ml, 26.88 mmol, 2.2 eq.). This was added with the Weinreb amide 3 (3.89 g, 24.43 mmol, 2.0 eq.) and washed with aqueous tartaric acid solution. The aqueous phase was extracted with diethyl ether, the combined organic phases were washed with saturated NaCl solution, dried over magnesium sulfate, and the solvents were removed. The resulting residue was purified using LC. Compound D was obtained in the form of an orange solid (0.1 g, 0.20 mmol, 1.6%).

EXAMPLE 5

Fluorescent Dye E

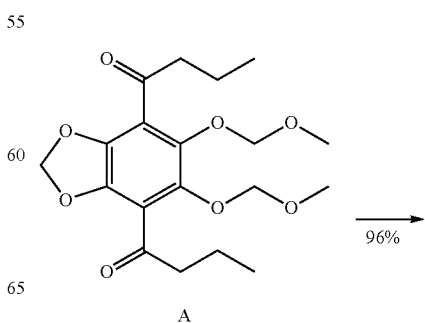

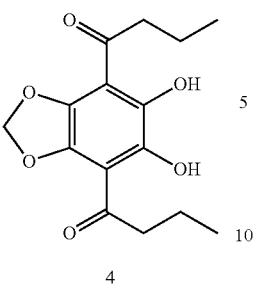

4

3807 mg (9.96 mmol) of compound A from Example 1 was dissolved in 80 ml of methanol and 1 ml of H$_2$O and added with a small amount of p-toluenesulfonic acid. The depositing red precipitate was made free of solvent and purified by means of LC to afford 2816 mg (0.48 mmol, 96%) of compound 4 in the form of dark red crystals.

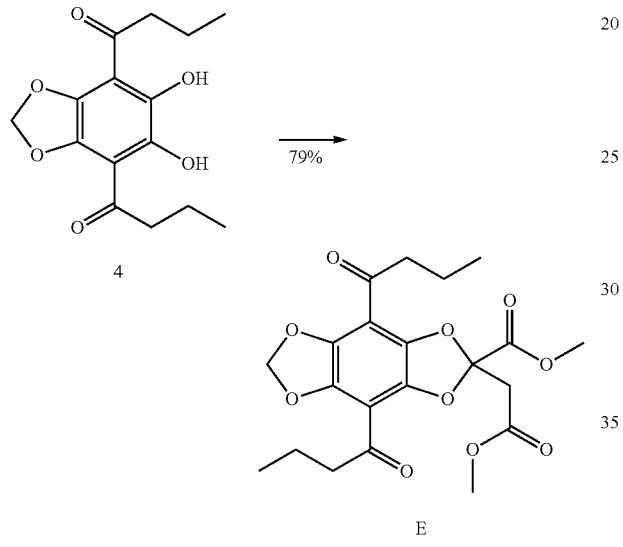

E 500 mg (0.43 mmol) of compound 4 was placed in 25 ml of dry dichloromethane. A catalytic amount of 1,4-diazabicyclo[2.2.2]octane and 241 mg (1.7 mmol) of dimethyl acetylenedicarboxylate were added. After completion of the reaction, 50 ml of 20% tartaric acid solution was added. This was extracted with Et$_2$O, the organic phases were washed with dilute HCl and NaCl solution, dried over MgSO$_4$, and the solvent was removed. Purification using LC afforded 582 mg (1.33 mmol, 79%) of compound E in the form of an orange solid.

EXAMPLE 6

Fluorescent Dye F

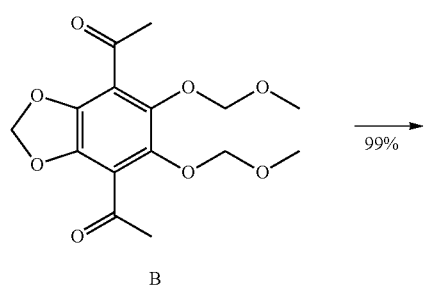

B

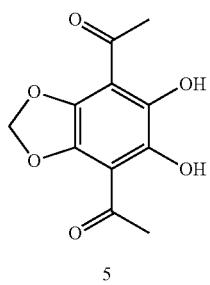

5

744 mg (2.28 mmol) of compound B from Example 2 was dissolved in 200 ml of methanol and 1 ml of H$_2$O and added with a small amount of p-toluenesulfonic acid. The depositing red precipitate was made free of solvent and purified by means of LC to afford 538 mg (2.26 mmol, 99%) of compound 5 in the form of dark red crystals.

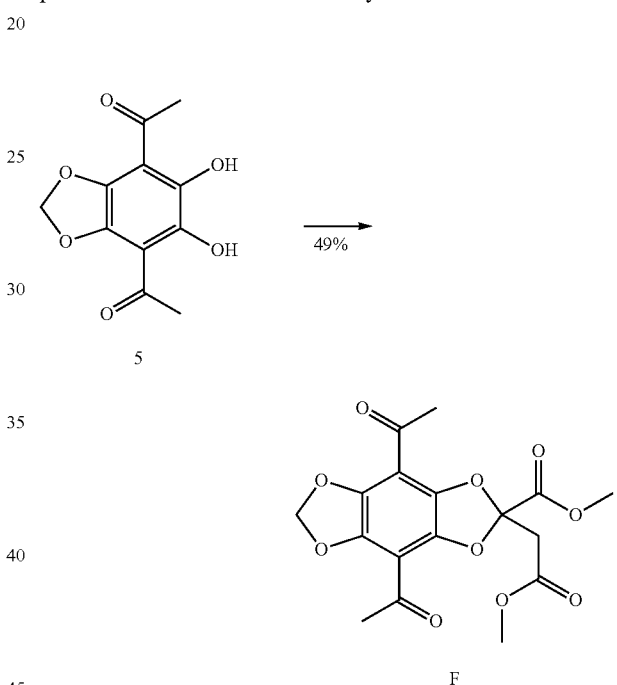

F 100 mg (0.43 mmol) of compound 5 was placed in 25 ml of dry dichloromethane. A catalytic amount of 1,4-diazabicyclo[2.2.2]octane and 73 mg (0.51 mmol) of dimethyl acetylenedicarboxylate were added. After completion of the reaction, 50 ml of 20% tartaric acid solution was added. This was extracted with Et$_2$O, the organic phases were washed with dilute HCl and NaCl solution, dried over MgSO$_4$, and the solvent was removed. Purification using LC afforded 80 mg (0.21 mmol, 49%) of compound F in the form of an orange solid.

7. Optical Properties of Compounds A-F

The absorption spectra and emission spectra of compounds A to F of Examples 1 to 6 were measured in a fluorescence spectrometer. FIG. 1 shows the spectra of compounds A-C and FIG. 2 the corresponding spectra of compounds D-F. The respective peaks of the absorption spectra and emission spectra were used to determine the excitation wavelength $\lambda_{abs}$ and emission wavelength $\lambda_{em}$, respectively, and the Stokes shifts $\Delta\lambda$ were calculated from the difference of the two.

Furthermore, the extinction coefficients $\epsilon$ and fluorescence quantum yields $\Phi_F$ were determined using suitable fluorescence standards, and the fluorescence lifetime $\tau_F$ was determined using time-dependent measurement of the $\lambda_{em}$ fluorescence decay function.

The determined fluorescence properties of compounds A-C and D-F are summarized in Tables 1 and 2.

FIG. 3 shows the correlation between Stokes shift $\Delta\lambda$ and fluorescence lifetime $\tau_F$ for the compounds A-F. Corresponding values for some commercially available fluorescent dyes are shown for comparison (PURETIME is a product name of AssayMetrics Ltd., 22 Angelica Way, Cardiff, CF14 9FJ, UK; ATTO is a product name of ATTO-TEC GmbH, Am Eichenhang 50, 57076 Siegen, Germany; BODIPY is a product name of Invitrogen Corporation, EvoQuest™ Laboratory Services, 5791 Van Allen Way, Carlsbad, Calif. 92008, USA). As is apparent from the illustration, none of the known fluorescent dyes has a long fluorescence lifetime of $\tau_F \geq 5$ ns in combination with a large Stokes shift of $\Delta\lambda \geq 50$ nm. In contrast, all fluorescent dyes according to the invention comply with these two criteria. In particular, each of the three fluorescent dyes A-C of general formula I has a Stokes shift of $\Delta\lambda \geq 150$ nm and a fluorescence lifetime $\tau_F \geq 5$ nm (for A and B the fluorescence lifetime is even $\tau_F \geq 15$ ns). Conversely, each of the three fluorescent dyes D-F of general formula II has a Stokes shift of $\Delta\lambda \geq 100$ nm at a fluorescence lifetime $\tau_F \geq 20$ ns.

These results confirm the outstanding fluorescence properties of the compounds according to the invention, demonstrating their specific suitability for use as fluorescent dyes, especially in biological and medical applications.

TABLE 1

Optical properties of dyes A-C (solvent: acetonitrile)

| Fluorophore | $\lambda_{abs}$ (nm) | $\lambda_{em}$ (nm) | $\Delta\lambda$ (nm) | $\epsilon$ (M$^{-1}$cm$^{-1}$) | $\tau_F$ (ns) | $\Phi_F$ | $\Phi_F \cdot \epsilon$ (M$^{-1}$cm$^{-1}$) |
|---|---|---|---|---|---|---|---|
| 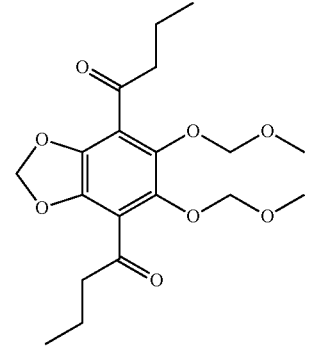<br>A | 332 | 503 | 171 | 2500 | 14.9 | 0.41 | 1030 |
| 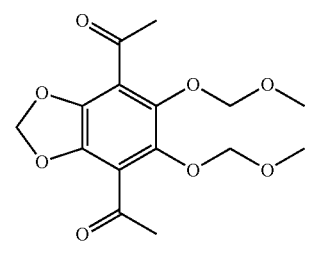<br>B | 343 | 518 | 175 | 1800 | 16.5 | 0.46 | 830 |
| 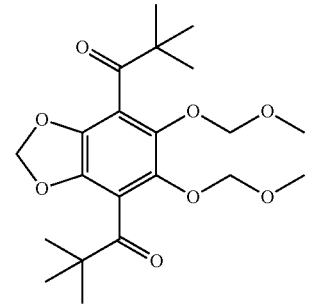<br>C | 302 | 492 | 180 | 3300 | 6.1 | 0.25 | 830 |

TABLE 2

Optical properties of dyes D-F (solvent: acetonitrile)

| Fluorophore | $\lambda_{abs}$ (nm) | $\lambda_{em}$ (nm) | $\Delta\lambda$ (nm) | $\epsilon$ (M$^{-1}$cm$^{-1}$) | $\tau_F$ (ns) | $\phi_F$ | $\phi_F \cdot \epsilon$ (M$^{-1}$cm$^{-1}$) |
|---|---|---|---|---|---|---|---|
| 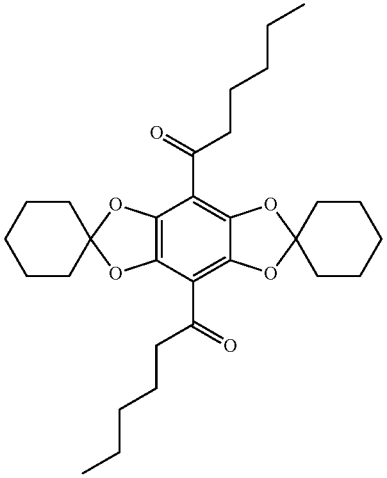 D | 443 | 547 | 104 | 4100 | 19.8 | 0.57 | 2300 |
| 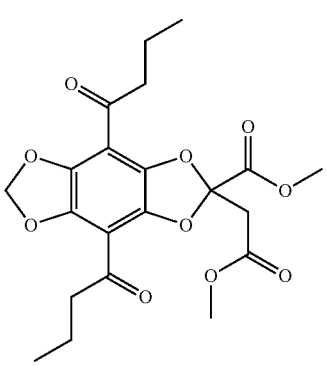 E | 424 | 535 | 111 | 4100 | 22.5 | 0.61 | 2500 |
| 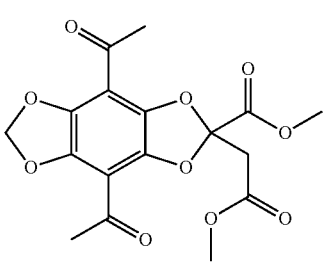 F | 423 | 532 | 109 | 4800 | 22.4 | 0.62 | 2980 |

The invention claimed is:

1. A fluorescent dye according to general formula I or II:

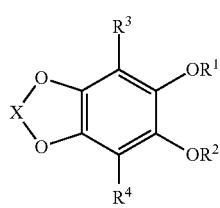

(I)

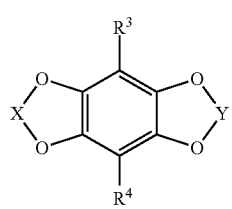

(II)

wherein $R^1$ and $R^2$ are independently selected from the group consisting of hydrogen or a branched or unbranched, saturated or unsaturated, aliphatic or aromatic, functionally substituted, or unsubstituted hydrocarbon radical, alkoxy radical, ether radical, alkoxyether radical, acyl radical, ketone radical, carboxylic acid radical, carboxylic ester radical, or aldehyde radical, wherein at least one of the $R^1$ or $R^2$ radicals is not hydrogen; $R^3$ and $R^4$ are independently selected from the group consisting of a $C_2$-$C_{20}$ acyl radical, a $C_2$-$C_{20}$ acylaryl radical, a $C_2$-$C_{20}$ acylalkenyl radical, a $C_2$-$C_{20}$ acylalkynyl radical or a nitro group, and the $R^1$ and $R^3$ radicals and/or $R^2$ and $R^4$ radicals in formula I can be bridged to each other; and X and Y independently represent a substituted or unsubstituted $C_1$ hydrocarbon radical or an N or S heteroatom.

2. The fluorescent dye according to claim 1, wherein the radicals $R^1$ and $R^2$ are selected to be the same and/or the radicals $R^3$ and $R^4$ are selected to be the same.

3. The fluorescent dye according to claim 1, wherein $R^1$ and $R^2$ independently represent a branched or unbranched, saturated or unsaturated, functionally substituted, or unsubstituted $C_1$-$C_{20}$ alkyl radical, $C_5$-$C_{20}$ aryl radical, $C_2$-$C_{20}$ alkenyl radical, $C_2$-$C_{20}$ alkynyl radical, $C_1$-$C_{20}$ alkoxy radical, $C_2$-$C_{20}$ ether radical, $C_2$-$C_{20}$ alkoxyether radical, $C_2$-$C_{20}$ acyl radical, $C_3$-$C_{20}$ ketone radical, $C_1$-$C_{20}$ carboxylic acid radical, $C_2$-$C_{20}$ carboxylic ester radical, or $C_1$-$C_{20}$ aldehyde radical.

4. The fluorescent dye according to claim 1, wherein both radicals $R^3$ and $R^4$ represent a $C_2$-$C_{10}$ acyl radical, a $C_2$-$C_{10}$ acylaryl radical, a $C_2$-$C_{10}$ acylalkenyl radical, or a $C_2$-$C_{10}$ acylalkynyl radical or a nitro group.

5. The fluorescent dye according to claim 1, wherein X and Y independently represent a substituted or unsubstituted $C_1$ hydrocarbon radical.

6. The fluorescent dye according to claim 1, wherein at least one of the radicals $R^1$ and $R^2$ is selected from the group consisting of a $C_1$-$C_{20}$ alkoxy radical, $C_2$-$C_{20}$ ether radical, and $C_2$-$C_{20}$ alkoxyether radical.

7. A fluorescent dye according to any of formulas A, B, C or G:

(A)

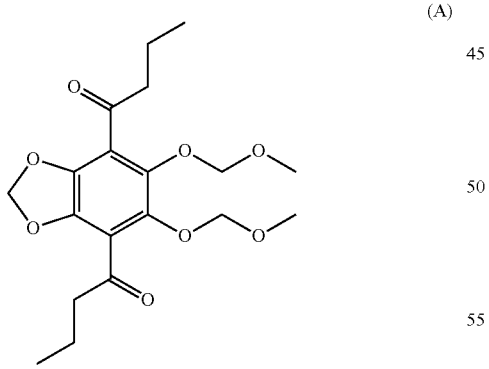

(B)

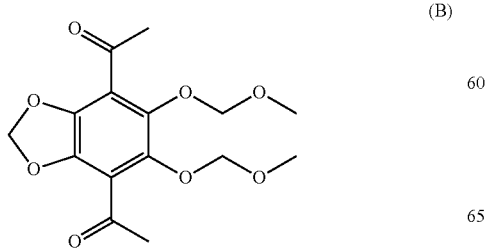

(C)

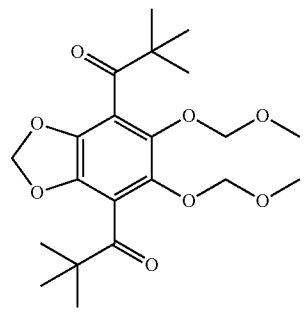

(G)

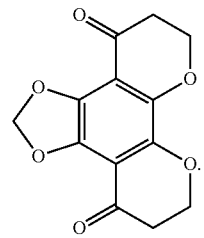

8. A fluorescent dye according to any of formulas D, E or F:

(D)

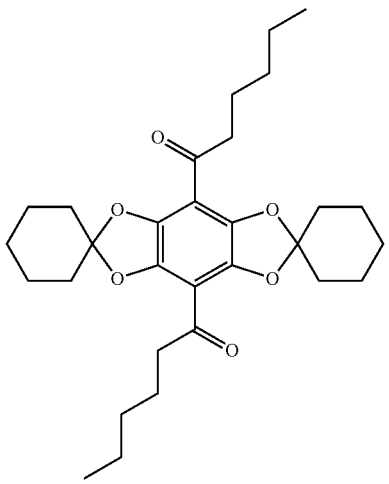

(E)

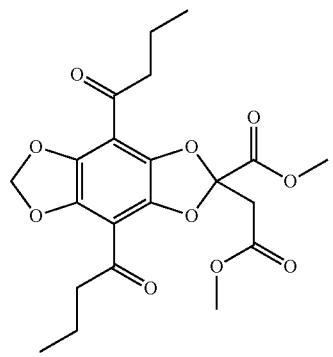

(F)

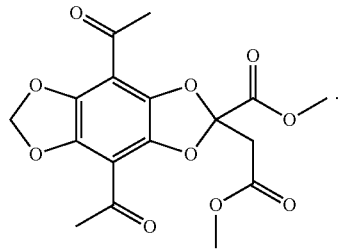

9. A conjugate comprising a fluorescent dye as claimed claim 1 and a biomolecule coupled to said fluorescent dye or a cell coupled to said fluorescent dye.

10. The conjugate according to claim 9, wherein the biomolecule is selected from the group consisting of proteins, peptides, nucleic acids, lipids and carbohydrates.

11. A conjugate comprising a fluorescent dye as claimed in claim 7 and a biomolecule coupled to said fluorescent dye or a cell coupled to said fluorescent dye.

12. The conjugate according to claim 11, wherein the biomolecule is selected from the group consisting of proteins, peptides, nucleic acids, lipids and carbohydrates.

13. A conjugate comprising a fluorescent dye as claimed in claim 8 and a biomolecule coupled to said fluorescent dye or a cell coupled to said fluorescent dye.

14. The conjugate according to claim 13, wherein the biomolecule is selected from the group consisting of proteins, peptides, nucleic acids, lipids, and carbohydrates.

15. The fluorescent dye according to claim 4, wherein at least one of the radicals $R^3$ and $R^4$ is a $C_2$-$C_{10}$ acyl group.

16. The fluorescent dye according to claim 1, wherein X and Y independently represent a $CH_2$ radical, $CHR^5$ radical or $CR^5R^6$ radical, and the radicals $R^5$ and $R^6$ can be bridged to each other to form a 3- to 6-membered spiro ring.

17. The fluorescent dye according to claim 1, wherein both $R^1$ and $R^2$ are selected from the group consisting of a $C_1$-$C_{20}$ alkoxy radical, $C_2$-$C_{20}$ ether radical, and $C_2$-$C_{20}$ alkoxyether radical.

18. The fluorescent dye according to claim 1, wherein at least one of the radicals $R^1$ and $R^2$ is selected from the group consisting of a $C_1$-$C_{10}$ alkoxy radical, $C_2$-$C_{10}$ ether radical, $C_2$-$C_{10}$ alkoxyether radical.

19. The fluorescent dye according to claim 4, wherein both $R^3$ and $R^4$ are a $C_2$-$C_{10}$ acyl group.

* * * * *